United States Patent [19]

Cohen

[11] 4,221,954
[45] Sep. 9, 1980

[54] HEATED MUFF

[76] Inventor: Florence Cohen, 6700 E. Thomas Rd., Scottsdale, Ariz. 85251

[21] Appl. No.: 896,726

[22] Filed: Apr. 17, 1978

[51] Int. Cl.² ............................................. H05B 1/00
[52] U.S. Cl. ....................................... 219/212; 2/66; 128/402; 219/527; 219/535
[58] Field of Search .............. 219/211, 212, 527, 528, 219/529, 535, 536, 549; 128/381, 379, 402, 411; 126/204; 2/66, 91, 208

[56] References Cited

U.S. PATENT DOCUMENTS 2,727,241  12/1955  Smith .................................. 2/66

FOREIGN PATENT DOCUMENTS 436503  10/1935  United Kingdom ..................... 128/411

Primary Examiner—C. L. Albritton
Attorney, Agent, or Firm—Roy L. Knox

[57] ABSTRACT

A hand warmer, particularly for simple therapeutic treatment or pain alleviation for the hands of arthritics, the warmer having the general configuration of a muff accommodating both hands of the user, the muff having a heated core which can be gently or firmly grasped by the user, inside an outer envelope of soft cloth or fur-like material which retains the heat, the core also having a covering of soft thermal material over a safety sheath and heat-distributive padding to prevent accidental contact with wiring or hot spots in the core.

3 Claims, 3 Drawing Figures

HEATED MUFF

BACKGROUND OF THE INVENTION

Heated gloves and mittens have been developed, and some patented, for warming the hands. These prior art devices have included variable temperature controls and both battery and house current operated models have been proposed. A recent patent, U.S. Pat. No. 3,869,594, employs a fluid container on the back of the hand, electrically heated by calrods immersed in the fluid. Another patent, U.S. Pat. No. 3,292,628, closer to the applicant's concept, discloses a glove with resistance heating wires on both top and bottom sides of the glove. U.S. Pat. No. 3,569,666 shows a glove heated by a unit at "the finger tip portion on the palm side". U.S. Pat. No. 3,621,191 discloses a heating wire embedded in a plastic liner, and U.S. Pat. No. 3,781,514 shows a similar concept employing a lattice structure permitting stretching of the glove. There exists a need, however, for a hand warmer which will economically and aesthetically permit a user to warm both hands, and all portions of the hands safely and comfortably while permitting maximum ease of withdrawal and re-entry of the hands.

SUMMARY OF THE INVENTION

As claimed, the instant invention fulfills the immediately abovementioned need, being a hand warmer having an outer, flexible tubular envelope with the general configuration of a muff having hand access openings at opposed ends, and a core, conceived as ordinarily heated by electricity, battery or line voltage, with a resistance element wound on an elongated tubular member and surrounded by heat-distributive padding, all enclosed in a safety sheath and a soft covering to be grasped by the hands of the user. The envelope and covering are conceived as being of soft cloth or fur-like material and the sheath is moisture proof. The elongated tubular member is adapted to house portions of the electric wiring and resistors required in making the heating variable. All parts of the warmer should be fire-resistant.

DETAILED DESCRIPTION OF A PREFERRED EMBODIMENT

Figure 1:
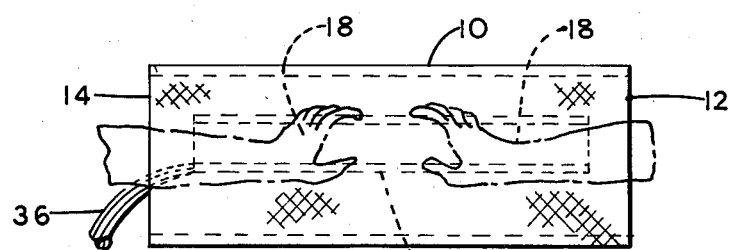
FIG. 1 is a side elevational view of the muff with the core represented in dash line, and indicating how the hands of the user are inserted through the openings at each end to grasp the heated core.
Figure 2:
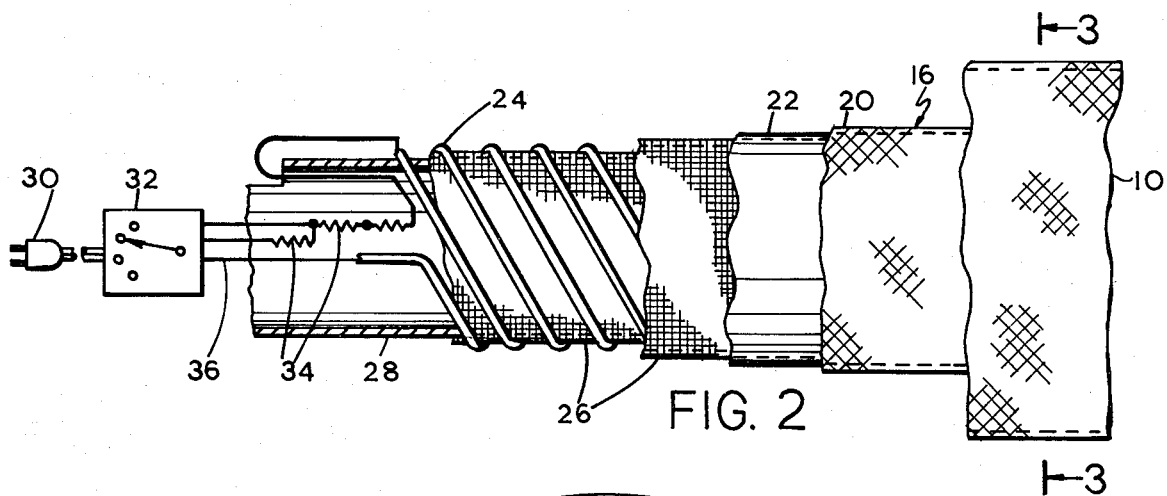
FIG. 2 is a fragmentary view on an enlarged scale, showing the muff with portions broken away to show the underlying parts, and with the electrical circuit shown diagrammatically.
Figure 3:
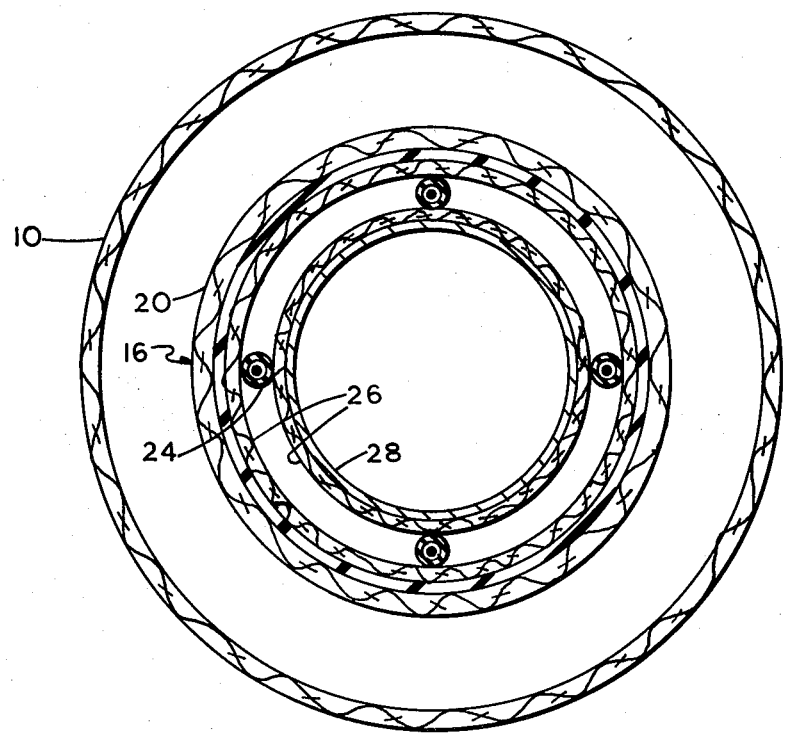
FIG. 3 is a still further enlarged cross sectional view taken on the line 3—3 in FIG. 2.

Application of moderate heat to the hands has long been recognized as helpful, at least in the relief of pain, by persons suffering from arthritis of the hands. This is the principal use of the instant invention. As indicated in the drawing, the muff comprises an elongated casing or envelope 10 which can be thought of as tubular but being of flexible thermal material such as soft cloth or fur-like material, the circular cross-sectional shape indicated in the drawing may not be maintained in use. The ends 12, 14 of the casing 10 are open.

Inside the casing 10 is the structure hereinafter referred to generally as the core 16. This core 16 is nearly as long as the casing 10 but much smaller in cross-section so that the hands 18, 18 of the user can be thrust through the open ends 12, 14 into the space between the core 16 and the casing 10. The hands may grasp the core with the thumbs opposing the fingers or as indicated in FIG. 1. The core will ordinarily be at least generally cylindrical and has a tubular covering 20 which fits reasonably snugly thereon, and this covering 20 may be of similar material as the casing 10 but in any case should be soft and comfortable to the hands. The casing 10 and covering 20 being easily separable from the portion of the core are preferably launderable.

Immediately inside the covering 20 is a safety sheath 22 which is of waterproof material and which also functions as a heat distributor. The safety sheath must also be electrically non-conductive and relatively impervious to moderate heating. The heating is accomplished by a resistance element 24 embedded in and covered by heat-distributive padding 26, the element 24 and padding 26 being wound upon a hollow elongated member 28, shown as a simple tube of form-retaining insulative material of a length only slightly less than the sheath 22. The padding may comprise, alternatively or in addition, a layer thereof on the inside and outside of the wound resistance element.

Finally, the resistance element 24 is connected, according to the technology employed in electric blankets and the like, to a source of energy such as a battery or, as illustrated to an electrical outlet by a plug 30. Variation of temperature within the muff is controlled by a multiple position switch 32, operated manually by the user, and wiring including resistors 34 in a three wire circuit 36, all according to prior art technique which incidentally may incorporate simple thermistors or thermostats units for more perfect temperature control. In this regard it is conceived that the instant muff may be made in small, unobtrusive battery-operated sizes for use in public, such as when the user is enjoying concerts and analogous occasions. In any case, the hollow elongated member 28 easily accomodates the current control units such as the resistors 34 and any necessary part of the circuit 36.

The operation of this invention will be obvious from a reading of the foregoing disclosure and further description would appear unnecessary. As mentioned above, the core may be grasped tightly or gently. If grasped tightly the enhanced direct transfer of heat to the hand results in the user feeling a greatly increased heating effect. If the hands are inserted in the heated muff with gentle grasping of the core, or no actual grasping, then a more moderate warming of the hands is achieved, resulting from containment of the heat within the muff by the casing 10. Of course, either only one or both hands may be inserted in the muff.

What I claim as new and desire to secure by Letters Patent, as an article of manufacture, is:

1. Structure with a hand-graspable heated core, comprising:
   (a) an elongated envelope of thermal material with hand access openings at opposite ends of the envelope, leading to the interior thereof;
   (b) a cylindrical core longitudinally slidably insertable into the interior of said envelope, and dimensioned and configured to be grasped by one or both hands of the user, at the user's option simultaneously, within said interior;
(c) means in said core to heat said core;
(d) whereby the core may be grasped gently for moderate warming or tightly for enhanced direct transfer of heat to the hand resulting in the user feeling a greatly increased heating effect;
(e) said core having a centrally elongated member fixed therein, a resistance element wound thereon, heat distributive padding of incombustible insulative material surrounding solid resistance element, and a safety sheath over said padding, said sheath being of material electrically non-conductive and moisture-proof.

2. Structure according to claim 1 wherein said cylindrical core is easily separable from said envelope and is only slightly less in length than said envelope, and said thermal material is soft flexible fabric to conform with the hands of the user.

3. Structure according to claim 1 wherein said core has a tubular, separable, launderable covering and said envelope is also launderable so that both portions likely to be soiled in use, namely said covering and said envelope, can be easily cleaned.

* * * * *